United States Patent [19]

Chen et al.

[11] Patent Number: 5,202,159
[45] Date of Patent: Apr. 13, 1993

[54] PREPARATION METHOD OF MICRODISPERSED TABLET FORMULATION OF SPRAY-DRIED SODIUM DICLOFENAC ENTERIC-COATED MICROCAPSULES

[75] Inventors: Li J. Chen, Hsin-Ying; Chun N. Chen, Chia-Yi; Shan Y. Lin, Taipei, all of Taiwan

[73] Assignee: Standard Chemical & Pharmaceutical Corp., Ltd., Taiwan

[21] Appl. No.: 636,121

[22] Filed: Dec. 31, 1990

[51] Int. Cl.$^5$ .................. A61K 9/20; A61K 9/26; B01J 13/20
[52] U.S. Cl. .................. 427/213.31; 264/4.3; 264/4.33; 264/4.6; 424/452; 424/461; 424/462; 424/465; 424/469; 514/825; 514/965
[58] Field of Search .................. 264/4.3, 4.33, 4.6; 427/213.31, 213.36; 424/452, 461, 462, 465, 469; 514/965, 825

[56] References Cited

U.S. PATENT DOCUMENTS

| | | | |
|---|---|---|---|
| 3,922,338 | 11/1975 | Estevenel et al. | 424/469 |
| 3,927,196 | 12/1975 | Hersh | 424/452 |
| 4,540,602 | 9/1985 | Motoyama et al. | 427/213.31 |
| 4,710,384 | 12/1987 | Rotman | 424/465 |
| 4,867,985 | 9/1989 | Heafield et al. | 424/461 |
| 4,867,987 | 9/1989 | Seth | 424/480 |
| 4,894,239 | 1/1990 | Nonomura et al. | 424/497 |
| 4,968,505 | 11/1990 | Okada et al. | 424/461 X |
| 4,980,170 | 12/1990 | Schneider et al. | 424/461 X |
| 5,009,897 | 4/1991 | Brinker et al. | 424/469 |

Primary Examiner—Richard D. Lovering
Attorney, Agent, or Firm—Cushman, Darby & Cushman

[57] ABSTRACT

A preparation method of sodium diclofenac enteric-coated microcapsules by spray drying technique comprising the steps of
(a) dissolving sodium diclofenac in an appropriate amount of distilled water;
(b) adding an effective amount of excipients to the above solution to form a suspension;
(c) adding methacrylic acid-ethyl acrylate copolymers (Eudragit L 30D) and polyethyleneglycol 6000 (PEG 6000) as the enteric-coating material to form a slurry;
(d) atomizing the slurry to form spray-dried powder;
(e) mixing the spray-dried powder with a mixture of microcrystalline cellulose (neocel) and pregelatinized starch (flo-starch); and
(f) compressing the powder mixture into a microdispersed enteric tablet.

The spray drying technique could be easily performed to prepare the enteric-coated microcapsules with aqueous latex polymer dispersion such as Eudragit L 30D as an enteric-coating polymer.

4 Claims, 5 Drawing Sheets

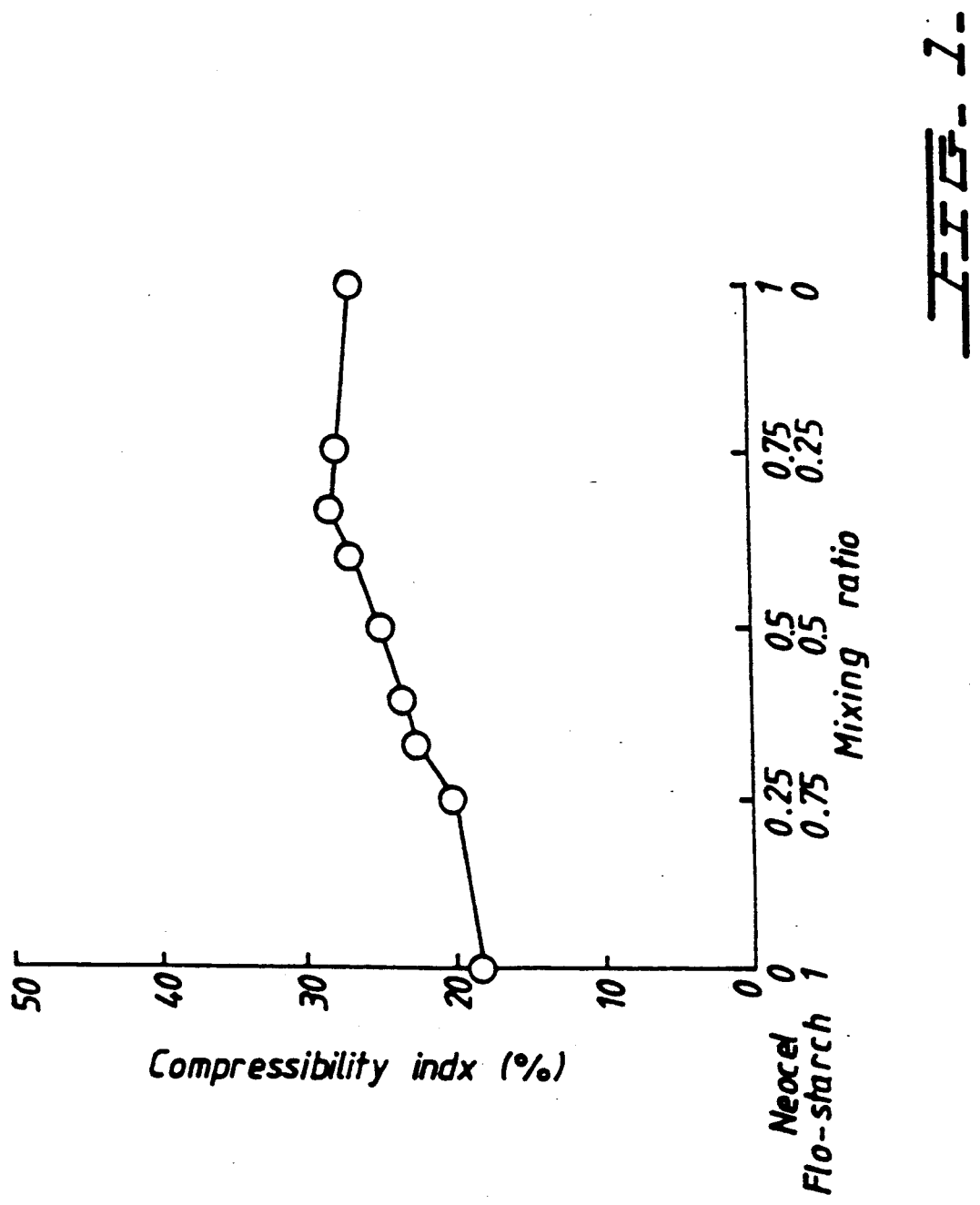

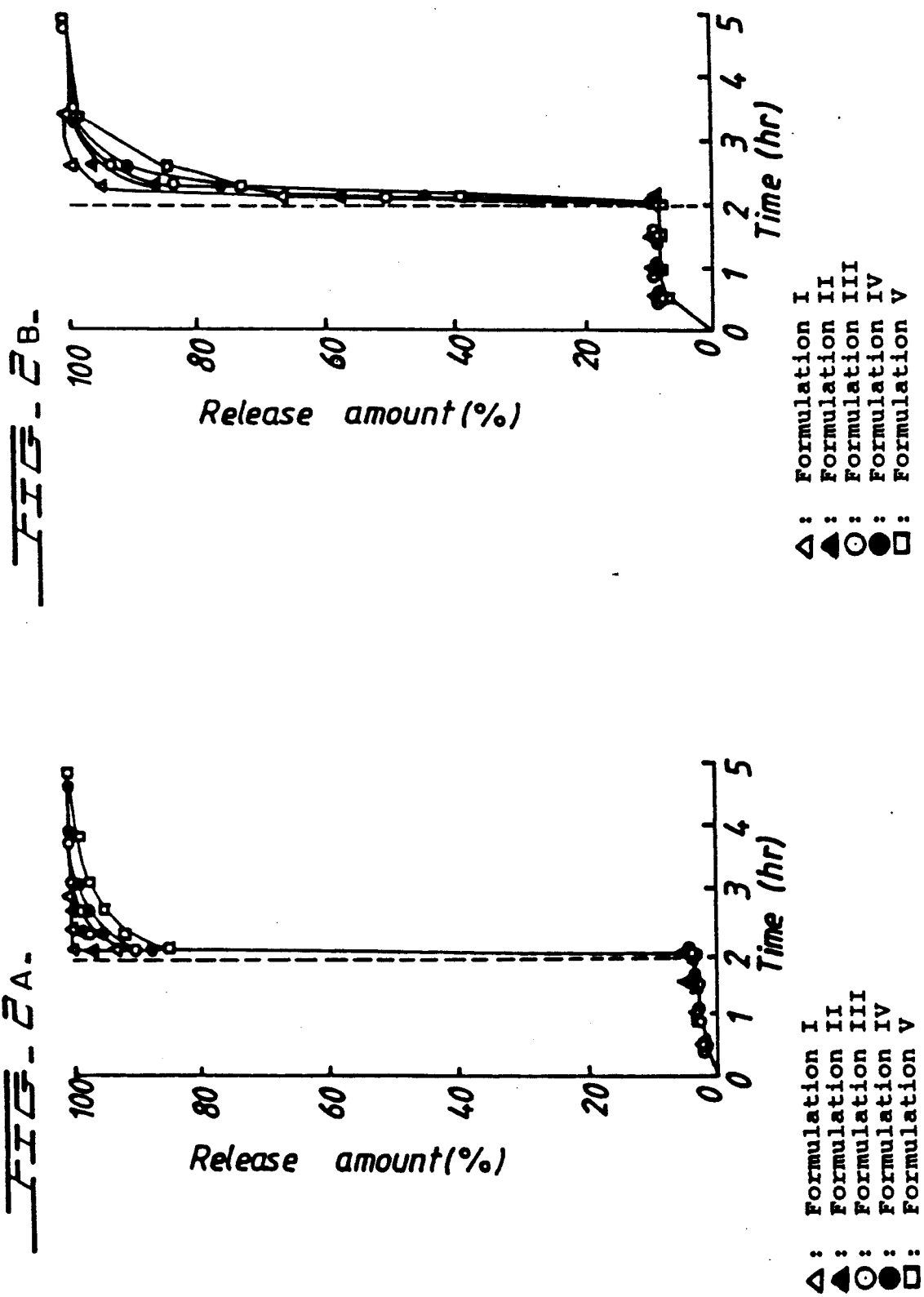

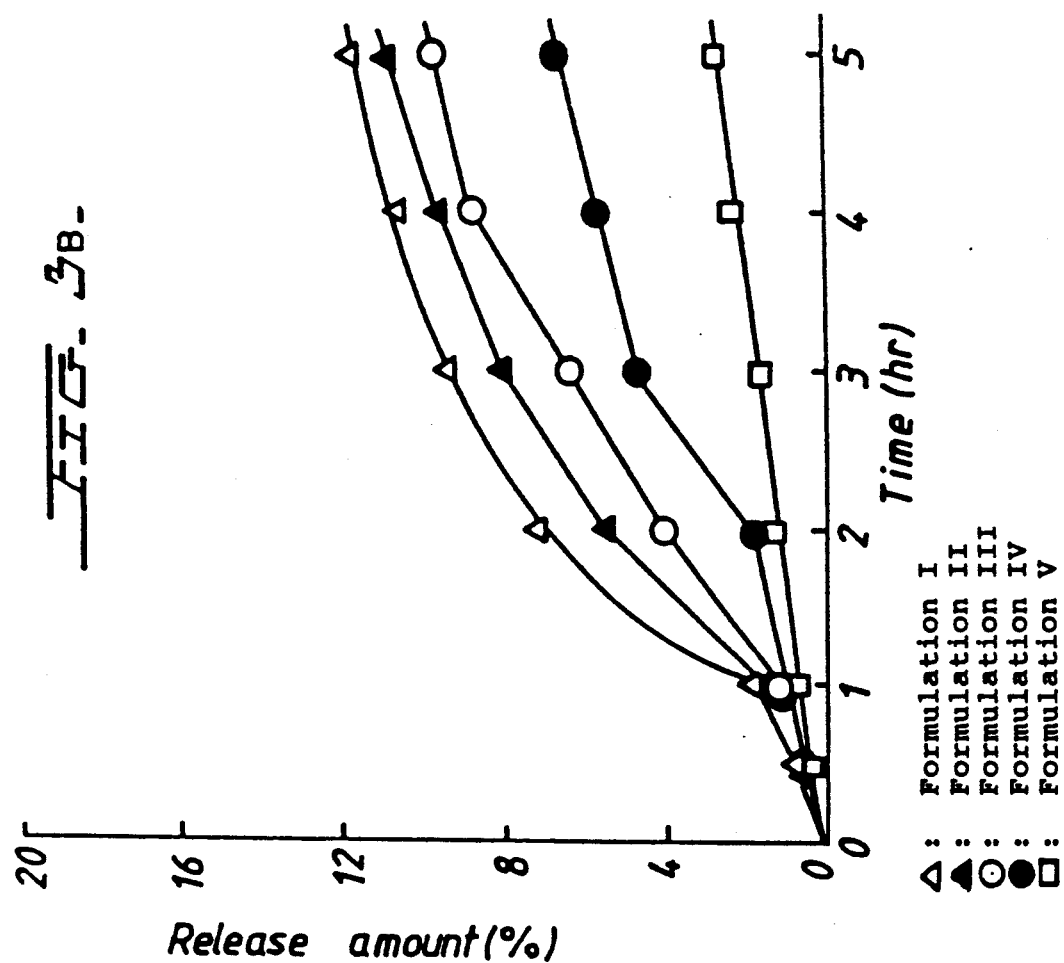
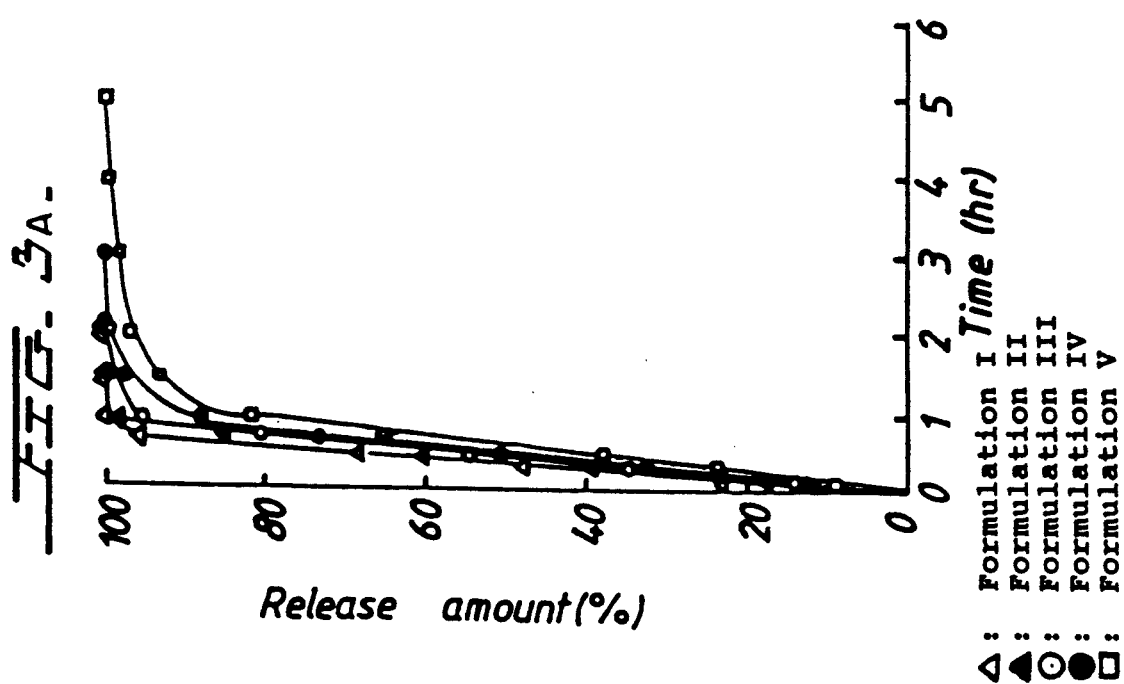

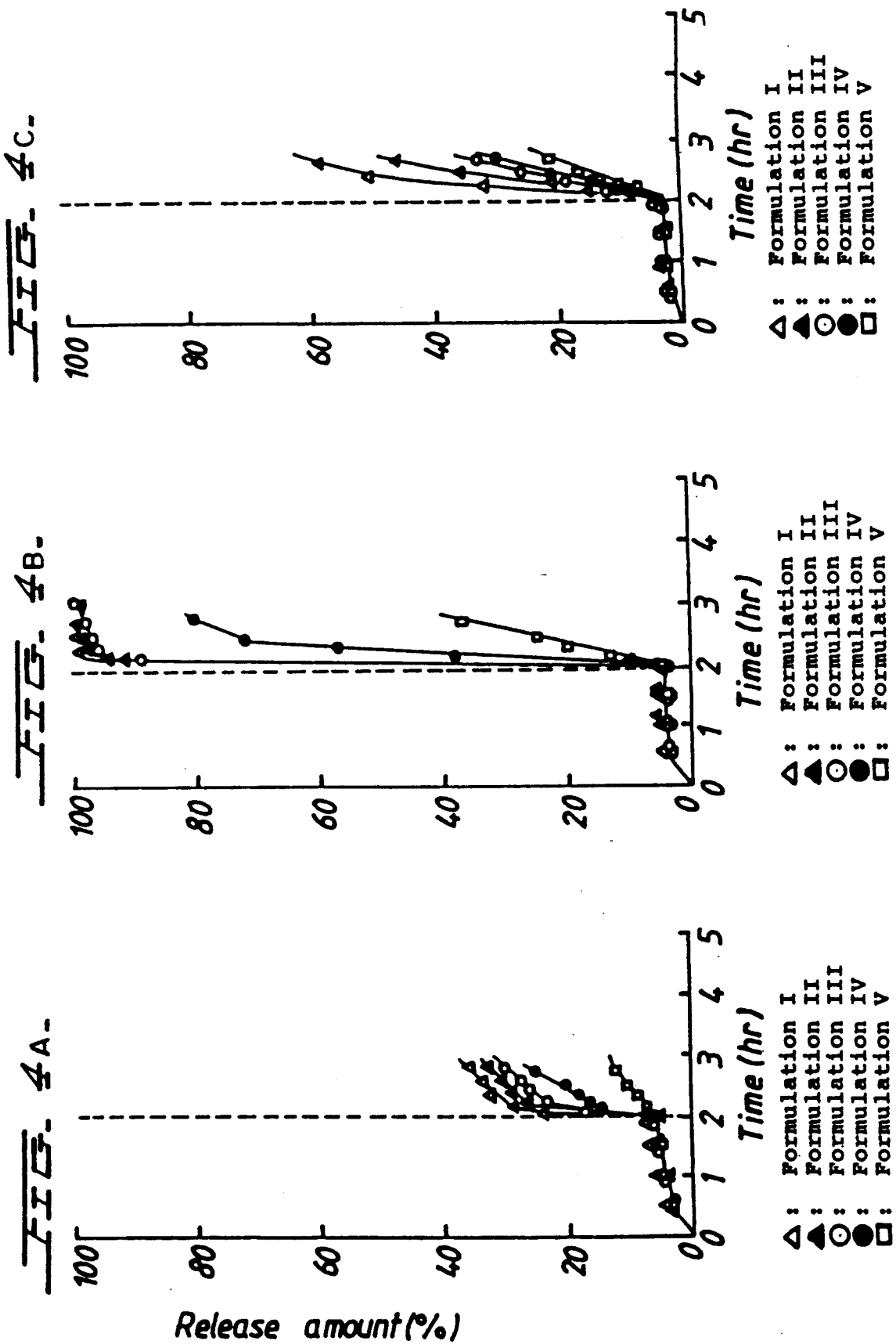

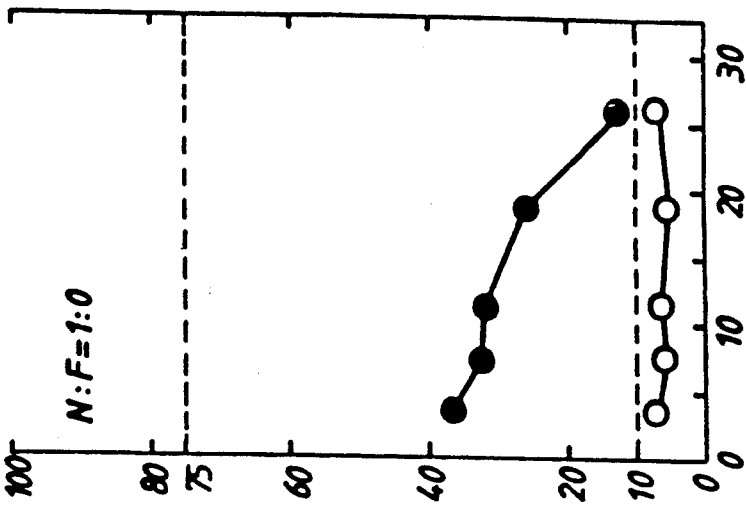

PREPARATION METHOD OF MICRODISPERSED TABLET FORMULATION OF SPRAY-DRIED SODIUM DICLOFENAC ENTERIC-COATED MICROCAPSULES

BACKGROUND OF THE INVENTION

The present invention relates to the preparation of sodium diclofenac enteric-coated microcapsules, in particular, the preparation method by spray drying technique with methacrylic acid-ethyl acrylate copolymers (Eudragit L 30D) as the enteric-coating material. The spray-dried powder was mixed with a mixture of microcrystalline cellulose (neocel) to pregelatinized starch (flo-starch) and was directly compressed into a tablet.

Generally, sodium diclofenac is a widely used nonsteroidal anti-inflammatory drug to treat rheumatoid arthritis,.osteoarthritis and ankylosing spondylitis. This has been disclosed in the following references, "J. R. Caldwell, Am. J. Med., 80, (Suppl. 4B), 43–46(1986), R. Altman, Am. J. Med., 80, (Suppl. 4B), 48–52 (1986), J. J. Calabro, Am. J. Med., 80, (Suppl. 4B), 58–63 (1986), and R. N. Brogden, R. C. Heel, G. E. Pakes, T. M. Speight and G. S. Avery, Drugs, 20, 24–48 (1984)". In order to eliminate its gastro-intestinal (GI) effect, the main adverse effect for patients after taking diclofenac, (which has been disclosed in the following references, "W. M. O'brien, Am. J. Med., 80, (Suppl. 4B), 70–80 (1986), R. E. Small, Clin. Pharm., 8, 545–558 (1989)"), effective enteric-coated products have been developed and commercialized. They may allow a drug dosage form to pass through the acid environment of the stomach, then to disintegrate immediately in the upper intestine, releasing the drug. Numerous studies have been conducted to differentiate the multiple units from the single unit of enteric-coated preparations and have been disclosed in the references, "H. Maekawa, Y. Takagishi, K. Iwamoto, Y. Doi, T. Ogura, M. Ito, K. Kitamura and H. Fujimoto, Jap. J. Antibiot., 30, 631–638 (1977), M. Nakano, M. Itoh, J. Kazuhiko, H. Sekikawa and T. Arita, Int. J. Pharm., 4, 291–298 (1980), J. P. Dechesne, Int. J. Pharm., 37, 203–209 (1982)". There are many advantages for the multiple units of enteric-coated products as compared with the single unit of enteric dosage forms. For example, the multiple units may distribute well over a large surface area, thus minimizing the risk of local damage or erosion as caused by the dumping effect of the single unit. Compared with the single unit, they are also less variable and less dependent on gastric transit time. They may attain more constant plasma levels, achieving a slow-release effect, giving a higher accuracy in reproducibility dose by dose, and causing less decrease of bioavailability. This have been disclosed in the following references, "H. Bechgaard, Pharm. Acta Helv., 28, 149–157 (1982), C. Eskilson, Manuf. Chemist, 56, (3) 33–36 (1985), J. P. Dechesne and L. Dellattre, Int. J. Pharm., 34, 259–262 (1987), and M. J. Story, J. Pharm. Sci., 66, 1495–1496 (1977)". In particular, a single unit of enteric-coated product may be significantly influenced by the physiological pH condition of the patients and the existing foods, leading to poor bioavailability due to the change of disintegration time, which has been disclosed in the following references, "E. Nelson, Clin. Pharm. Ther., 4, 283–292 (1963), H. Maekawa, Y. Takagishi, Y. Doi and K. Iwamoto, Yakuzaigaku, 30, 94–99 (1970), G. T. Luce, Manuf. Chemist, 49, (7) 50–52, 67 (1978)". Therefore, the microdispersed or multiple-unit enteric-coated products were recently developed, which is well-known from references "J. P. Dechesne, Int. J. Pharm., 37, 203–209 (1982), C. Eskilson, Manuf. Chemist, 56, (3) 33–36 (1985), J. P. Dechesne and L. Dellattre, Int. J. Pharm., 34, 259–262 (1987), and C. D. Herzfeldt, A. Zimmer and R. Brehm, Pharm. Ind., 49, 948–951 (1987)". A spray drying aqueous formulation to prepare the enteric-coated microcapsules has been disclosed in the reference "H. Takenaka, Y. Kawashima and S. Y. Lin, J. Pharm. Sci., 69, 948–951 (1980)". Moreover, some interactions between the enteric-coating material and the drug during spray drying have been found, but it would not occur if wet granulation was used to prepare enteric-coated granules. This has been disclosed in the references "H. Takenaka, Y. Kawashima and S. Y. Lin, J. Pharm. Sci., 70, 1256–1260 (1981), and S. Y. Lin and Y. Kawashima, Pharm. Res., 4, 70–74 (1987)."

Recently, an aqueous polymeric latex or pseudolatex as enteric-coating material has been used for coating, to replace the organic solvent system, which has been disclosed in the references, "A. M. Mehta, M. J. Valazza and S. E. Abele, Pharm. Technol., 10, 46, 48–51, 53, 55–56 (1986), F. Gumowski, E. Doelker and R. Gurny, Pharm. Technol., 11, (2) 26–32 (1987)". Although the latter system offers some processing advantages such as low heat of vaporization, stability of water soluble or moisture-sensitive drugs and short processing time, safety precaution, environmental pollution and economic advantages have made the use of water more attractive and convenient when it was used as a solvent. The aqueous polymers often used for enteric coating are methacrylic acid-ethyl acrylate copolymers (Eudragit L 30D ), cellulose acetate phthalate (Aquateric) and polyvinyl acetate phthalate (Coateric), which has been disclosed in the reference "K. S. Murthy, N. A. Enders, M. Mahjour and M. B. Fawzi, Pharm. Technol., 10, (10) 36–46 (1986)". These aqueous polymers are insoluble in acidic media, but dissolve rapidly when the coating material is in contact with neutral or weak alkaline solution. Because water has a higher heat of vaporization, the appropriate equipment must be selected to offer a good drying efficiency. Fluid-bed dryer and coating pan are more often used than spray dryer to coat tablets or pellets with aqueous polymeric system in preparing sustained-release or enteric-coated products.

BRIEF DESCRIPTION OF THE DRAWINGS

The present invention will be further explained with reference to the annexed drawings, wherein FIG. 1 is a graph showing the compressibility index of the mixture of neocel to flo-starch, FIG. 2 are graphs showing sodium diclofenac released from the spray-dried product (A) and the powdered mixtures of excipients (N:F=1:1) and spray-dried product (B) in pH changed dissolution medium, the dotted line on the graphs indicate the pH change, FIG. 3 are graphs showing the dissolution profiles of sodium diclofenac tablets made by the mixture of excipients (N:F=1:1) and spray-dried products in distilled water (A) and 0.1N HCl solution (B), FIG. 4 are graphs showing the dissolution profiles of sodium diclofenac tablets made by the mixtures of spray-dried products and excipients, whose weight ratio of neocel (N) to flo-starch (F) is (A) N:F=0:1, (B) N:F=1:1, (C) N:F=1:0, and FIG. 5 are graphs showing the assessment of the release amounts of sodium diclofenac from tablets made from the mixtures of spray-dried products and excipients whose weight ratio of neocel (N) to flo-starch (F) is (A) N:F=0:1, (B) N:F=1:1 and (C) N:F=1:0, by using the criteria specified in USP XXI, "o" representing release amount in acidic phase and "o" representing release amount in buffer phase, the dotted line indicates the criteria specified in USP XXI Acceptance Table for enteric-coated article.

DETAILED DESCRIPTION OF THE PRESENT INVENTION

The present invention relates to a preparation method of sodium diclofenac enteric-coated microcapsules by spray drying technique comprising the steps of (a) dissolving sodium diclofenac in an appropriate amount of distilled water;

(b) adding an effective amount of excipients to the above solution to form a suspension;

(c) adding Eudragit L 30D and polyethyleneglycol 6000 (PEG 6000) as the enteric-coating material to form a slurry;

(d) atomizing the slurry to form spray-dried powder;

(e) mixing the spray-dried powder with a mixture of neocel and flo-starch; and (f) compressing the powder mixture into a microdispersed enteric tablet.

In accordance with the present invention, the spray drying technique to prepare enteric-coated microcapsule with aqueous acrylic latex was used. The powder properties of the spray-dried powder were determined. Tablet formulation with enteric-action was designed by mixing the spray-dried products with the mixture of neocel and flo-starch, and compressing them to form a microdispersed enteric tablet. The effect of different weight ratios of neocel to flo-starch (1:0, 1:1, 0:1) on the dissolution behavior of microencapsulated tablets with enteric action was also estimated.

The micromeritic properties of the spray-dried powder and the mixed powder for tableting were investigated. The flowability of the spray-dried powder was poor but improved after incorporating the excipients. The release rate of sodium diclofenac from the spray-dried powder, the mixed powder before tableting and tablets were carried out in 0.1N HCl solution, pH 6.8 phosphate buffer solution, distilled water and pH changed medium. The spray-dried powder, the mixed powder before tableting and the tablets all exhibited enteric-action property. The amount of sodium diclofenac releasing from the enteric tablets could meet the USP XXI acceptable specification for enteric-coated articles, which depended on the weight ratio of neocel to flo-starch. This ratio of 1:1 was more acceptable than to be 1:0 or 0:1

The following example is offered to aid in understanding of the present invention and is not to be construed as limiting the scope thereof.

EXAMPLE

Materials

The following materials were used in this example:

Sodium diclofenac (commercially available from Syn-Tech Chem. & Pharm. Co., Ltd., Hsin-Ying, Taiwan, ROC), Eudragit L 30D (commercially available from Rohm Pharm, Darmstadt, West Germany), neocel (microcrystalline cellulose, commercially available from Cheng Chyi Co. Ltd., ROC), and pure flo-starch (pregelatinized starch, commercially available from CPC Intern. Co., Australia) were used. All other excipients and reagents were available on the market.

PREPARATION OF SPRAY-DRIED PRODUCTS

The following Table I shows the spray drying formulations. Sodium diclofenac was dissolved in distilled water, and the appropriate amount of excipients were added to the solution to form a suspension and finally comix with Eudragit L 30D and its plasticizer—PEG 6000. The slurries were fed by a roller pump to the spray dryer (GA 32, Yamato Sci. Co. Ltd., Japan) and atomized into a drying chamber by a spray nozzle. The spray dryer was operated under the following conditions: inlet temperature: 160 5° C., outlet temperature: 80 5° C., drying air: 0.40 m$^3$/min and atomizing air: 1.0 kgf/cm$^2$. The yields of all spray dried products are >84%. The drug entrapped in each spray-dried product is listed in the following Table II.

TABLE I

Formulations for preparation of enteric-coated microcapsules by spray drying technique
Spray drying formulations (%)

| Components | I | II | III | IV | V |
|---|---|---|---|---|---|
| Sodium diclofenac | *37.50 | 37.50 | 37.50 | 37.50 | 37.50 |
| Eudragit L 30D | 3.75 | 7.50 | 11.25 | 18.75 | 26.25 |
| PEG 6000 | 2.50 | 2.50 | 2.50 | 2.50 | 2.50 |
| Aerosil | 6.25 | 6.25 | 6.25 | 6.25 | 6.25 |
| Soluble starch | 30.00 | 26.25 | 22.50 | 15.00 | 7.50 |
| Lactose | 25.00 | 25.00 | 25.00 | 25.00 | 25.00 |
| Symbols | (△) | (▲) | (○) | (●) | (□) |

*Additional 5% of sodium diclofenac was added

TABLE II

Micromeritic parameters of powdered and tableted spray-dried powders

| Parameters | I | II | III | IV | V |
|---|---|---|---|---|---|
| Powdered spray-dried powders | | | | | |
| Bulk density | 0.2697 | 0.2351 | 0.2172 | 0.2566 | 0.2238 |
| Tapping density | 0.5226 | 0.5007 | 0.4594 | 0.5237 | 0.4360 |
| Compressibility index (%) | 48.39 | 53.05 | 52.72 | 51.01 | 52.68 |
| a | 0.5382 | 0.5764 | 0.5938 | 0.5608 | 0.5897 |
| b | 0.0178 | 0.0182 | 0.0186 | 0.0185 | 0.0184 |
| Drug content (%) | 34.41 ± 1.34 | 32.23 ± 1.08 | 28.15 ± 0.97 | 25.56 ± 1.01 | 24.02 ± 0.89 |
| Tableted spray-dried powders* | | | | | |
| Bulk density | 0.3005 | 0.2969 | 0.3216 | 0.3184 | 0.2839 |
| Tapping density | 0.5961 | 0.5568 | 0.5655 | 0.5795 | 0.4986 |
| Compressibility index (%) | 49.59 | 46.68 | 43.12 | 45.05 | 43.06 |
| a | 0.5238 | 0.4873 | 0.4506 | 0.4721 | 0.4516 |
| b | 0.0448 | 0.0615 | 0.0604 | 0.5000 | 0.0461 |
| H (kg) | 19.04 ± 1.92 | 20.36 ± 1.76 | 19.32 ± 1.48 | 17.34 ± 1.13 | 17.44 ± 1.91 |

*The mixture of spray-dried powders and other excipients
**a and b are the parameters of Kawakita equation
***H is the hardness of tablets

MICROMERITIC PROPERTIES OF SPRAY-DRIED PRODUCTS

Packing property of the spray-dried products and the mixed powder before tableting was measured by a tapping powder method. Bulk density ($p_o$), tapping density ($p_t$) and compressibility index ($p_t-p_o/p_t$) were obtained, as listed in Table II. The Kawakita equation was used to estimate the packing property.

$$N/c = 1/ab + N/a \quad (1)$$

$$c = (Vo - Vn)Vo \quad (2)$$

where a and b are constants representing the proportion of consolidation at the closest packing attained and packing velocity index, respectively. N is the number of taps, Vo is the volume of powder in a measuring cylinder at the loosest packing, and Vn is the volume after the Nth tapping.

The compressibility index of the different weight ratio of neocel to flo-starch without drug was also investigated. The shape and surface topography of the excipients and the spray-dried products were observed by a scanning electron microscopy (S-520, Hitachi, Japan).

PREPARATION OF TABLETS

The spray-dried products containing sodium diclofenac equivalent to 25 mg were mixed with the mixture of neocel and flo-starch in a vinyl bag. The weight ratio of neocel to flo-starch (N:F) was 1:0, 1:1 or 0:1. After adding aerosil (1.5%), talc (1.5%) and magnesium stearate (1%), the mixed powder was directly tableted on a rotary tableting machine equipped with a concave punch. The tablet weighed 150 mg, and the thickness and diameter of tablet were 3.33 mm and 8.0 mm, respectively. The hardness of tablets was determined by hardness tester (NT-1M, Toyama SanGyo Co. Ltd., Japan).

DISSOLUTION STUDIES

The dissolution rates of the spray-dried products, the mixed powder before tableting and the tablets were determined using USP XXI Apparatus 2 at 37 0.5° C. with paddle, and rotation was set at 50 RPM. The dissolution medium was 0.1N HCL solution, pH 6.8 phosphate buffer solution and water (pH 5.7). In order to simulate the pH change of GI tract, pH changed dissolution procedure specified in USP XXI/NF XVI for enteric-coated articles, Method A, was followed: 2 hours of exposure to 750 ml of 0.1N HCL solution followed by testing in 1000 ml of pH 6.8 phosphate buffer solution adjusting with 250 ml of 0.20 M tribasic sodium phosphate solution. The releasing amount of sodium diclofenac was periodically determined by UV spectrophotometer (UV-320, Jasco, Japan). Voltaren and Voren tablets were also investigated as a comparison. The mean of six tablets was calculated.

Solid particles could be directly formed by spray drying the droplets. Since this technique combined the drying and agglomeration processes into one step, it may be time and cost saving, and under better process control, which has been disclosed in the references "S. Y. Lin and Y. H. Kao, Int. J. Pharm., 56, 249-259 (1989), H. Seager and C. B. Taskis, Manuf. Chemist, 47, (12) 28-38 (1976), and H. Seager, Manuf. Chemist, 48, (4) 25-35 (1977)". The surface of the spray-dried powder seemed to be all covered with polymeric materials, since the spray-dried products were capable of retarding drug release below 10% for two hours in 0.1N HCL solution (FIG. 4). Apparently, there was no significant difference in their superficial topographies, although Eudragit L 30D used was different in amount. Spherical particles with smooth surface or some surface shrinkages and folds were observed. The shrinkages of the wall were due to the higher drying temperature that caused the entrapped air bubbles to expand considerably but to be offset partially by the loss of water. The deep identations in the microcapsules were also found occasionally, which was probably the result of water loss from the drying drop during the early stage of processing, which has been disclosed in the reference "M. Rosenberg, Y. Talmon and I. J. Kopelman, Food Microstructure, 7, 15-23 (1988)".

Results shown in Table II of measurement of bulk density and compressibility index suggest that all the spray-dried materials are likely to have poor flow characteristics, because of the low value of bulk density and high value of compressibility index. The microstructure and the extremely small particles of the spray-dried products might result, in lower bulk density and higher porosity, leading to the poor flow property of the spray-dried powder. However, the poor flowability of spray-dried products could be improved by adding the excipients used for direct tableting. Since the compressibility index of the mixture of neocel to flo-starch was less than 30%, as shown in FIG. 1, the flowability of the tableted mixtures was hopefully improved. The parameters "a" and "b" of Kawakita equation were also decreased and increased, respectively, by adding the excipients into the spray-dried products, as shown in Table II. The low value of "a" and high value of "b" suggest a better flowability and packability of the powders. Spherical particles of the spray-dried products were distributed and embedded into the excipient mixture, and the wall material of the spray-dried particles acted as a dry binder to combine the excipients to form a hard tablet. Thus, these tablets were so hard to be range in 17-20 kg, but the hardness of polymer-free tablets was only about 8-10 kg.

The pH changed dissolution profiles of spray-dried powder and the mixed powder before tableting (N:F=1:1) are shown in FIG. 2. The release rate of both powder products was relatively slow in acidic pH media within the initial 2 hrs. After tribasic sodium phosphate was added, the medium pH changed from being acid to 6.8 and the release rate of drug increased rapidly. The other powdered mixtures, whether N:F was 1:0 or 0:1, had the same release behavior. This suggests that all the spray-dried powders were thoroughly encapsulated in enteric-coating polymer and possessed enteric-action property. The results of dissolution study also indicate that the release rate in pH 6.8 medium can vary with the amount of Eudragit L 30D added. The more the Eudragit L 30D used, the slower the release of drug.

The cumulative amount of sodium diclofenac releasing from tablets (N:F=1:1) in distilled water (pH 5.7) and 0.1N HCL solution is shown in FIG. 3. The tablet was immediately disintegrated to fine particles in distilled water and started to release, leading to the release of more sodium diclofenac (>90%) after one hour of dissolution, probably because the Eudragit L 30D was soluble at pH 5.5 and because the dissolution of sodium diclofenac could make a higher concentration of ionic strength in the dissolution medium. On the other hand, when the tablet (N:F=1:1) was exposed to the simulated gastric acid (0.1N HCL solution), it did not disintegrate and showed considerably slower release behavior after up to 5 hours, only 2-11% of the drug was released. The releasing amount of sodium diclofenac also depended on the levels of Eudragit L 30D used in the spray drying formulations. This indicates that the more the Eudragit L 30D used, the slower the release rate of the tablet in simulated gastric acid, in other words, the enteric-coating action depends on the amount of Eudragit L 30D used in spray drying formulation. The influence of the weight ratio of neocel to flo-starch (N:F=0:1, 1:1, 1:0) on the release rate of sodium diclofenac enteric tablets in pH changed medium is shown in FIG. 4. When the weight ratio of N:F in the tablet was 0:1, the amount of sodium diclofenac releasing from the tablets was less than 10% in 0.1N HCl solution two hours later, and only 15-40% of release amount could be obtained although medium pH changed to pH 6.8 for one hour. Perhaps the tablet did not disintegrate and therefore resulted in a lower release. For the same reason, the release amount of sodium diclofenac from the tablets prepared with the 1:0 ratio of N:F also exhibited only 20-60% of release amount in pH 6.8 phosphate medium. The weight ratio of N:F was 1:1, however, the release amount of drug in the pH 6.8 phosphate solution was larger than 80% except for formulation V. The rapid disintegration of the tablets after the shift of pH might be responsible for this higher dissolution rate. Being independent of such weight ratio, the release amount of sodium diclofenac from the tablets in pH 6.8 phosphate solution still depended on the amount of Eudragit L 30D used.

The desired release amount of sodium diclofenac enteric tablets must conform to USP XXI specification: no individual value should exceed 10% when dissolved in acid phase after 2 hours of operation, and in each unit not less than 75% should be released in buffer solution after continuous operation on the apparatus for 45 minutes. Thus the dissolved amount of sodium diclofenac enteric tablet determined by mixing the spray-dried products with the different weight ratio of neocel to flo-starch is summarized in FIG. 5. Apparently that the sodium diclofenac tablet made from the mixture of spray-dried products with neocel or flo-starch did not meet the USP XXI criteria. The releasing amount of sodium diclofenac was less than 75% in buffer phase after 45 min, but 2 hrs later this amount became less than 10% in acid phase. In the tablet prepared with the spray-dried products and mixture of neocel and flo-starch (N:F=1:1), the dissolved sodium diclofenac made from formulation I or II was more than 75% in buffer solution, but their initial dissolved amount exceeded 10%, thus failing to conform to the USP criteria. In the mean time, the releasing amount of sodium diclofenac tablet made from formulation V also did not meet the requirements of USP XXI since the dissolved level was less than 75%, although the release amount was less than 10% in acidic phase. On the other hand, the tablets prepared by formulations III and IV were found to meet the USP XXI criteria well in both acid phase and buffer phase. The released amount was not only less than 10% in acid phase but also more than 75% in buffer phase.

This investigation demonstrates that the spray drying technique could be easily performed to prepare the enteric-coated microcapsules with aqueous latex polymer dispersion such as Eudragit L 30D as an enteric-coating polymer. The feasibility for preparing sodium diclofenac enteric tablets by mixing the spray-dried enteric-coated microcapsules with 1:1 mixture of neocel to flo-starch is successfully achieved. All the spray-dried powder and the tablets made from such powder with the mixture of neocel to flo-starch show some resistance to the simulated gastric acid and then release the drug more rapidly in pH 6.8 buffer solution. The weight ratio of neocel to flo-starch plays an important role in adjusting the amount of sodium diclofenac releasing from enteric tablet to meet the criteria of enteric-coated articles as specified in USP XXI.

The invention has been described in detail including the preferred embodiments thereof. However, it will be appreciated that those skilled in the art, upon consideration of this disclosure, may made modifications and improvements within the spirit and scope of this invention.

We claim:

1. A preparation method of microdispersed tablet formulation with sodium diclofenac enteric-coated microcapsules by spray drying technique comprising the steps of
   (a) dissolving sodium diclofenac in an appropriate amount of distilled water;
   (b) adding an effective amount of excipients to the above solution to form a suspension;
   (c) adding methacrylic acid-ethyl acrylate copolymers and polyethyleneglycol 6000 as the enteric-coating material to form a slurry;
   (d) atomizing the slurry to form spray-dried powder;
   (e) mixing the spray-dried powder with a mixture of microcrystalline cellulose and pregelatinized starch; and
   (f) compressing the powder mixture into a microdispersed enteric tablet.

2. The preparation as set forth in claim 1, wherein atomizing is operated at inlet temperature of about 160° C. an outlet temperature of 80° C., and the speed of the drying air being 0.40 m/min and the atomizing air being 1.0 kgf/cm.

3. The preparation as set forth in claim 1, wherein the mixture of microcrystalline cellulose to pregelatinized starch is 1:1.

4. The preparation as set forth in claim 1, wherein the methacrylic acid-ethyl acrylate copolymers is an aqua emulsion.

* * * * *